United States Patent
Carter et al.

(10) Patent No.: US 9,687,589 B2
(45) Date of Patent: Jun. 27, 2017

(54) OXYGENATED THREE-DIMENSIONAL MATRIX FOR BONE GROWTH

(71) Applicant: THERACELL, INC., Northridge, CA (US)

(72) Inventors: Andrew J. Carter, Stow, MA (US); Nelson L Scarborough, Andover, MA (US); Frank M. Phillips, Highland Park, IL (US); Stephen H. Hochschuler, Paradise Valley, AZ (US); Bradley Patt, Northridge, CA (US)

(73) Assignee: THERACELL, INC., Northridge, CA (US)

( * ) Notice: Subject to any disclaimer, the term of this patent is extended or adjusted under 35 U.S.C. 154(b) by 0 days.

(21) Appl. No.: 14/760,187

(22) PCT Filed: Jan. 13, 2014

(86) PCT No.: PCT/US2014/011359
§ 371 (c)(1),
(2) Date: Jul. 9, 2015

(87) PCT Pub. No.: WO2014/110537
PCT Pub. Date: Jul. 17, 2014

(65) Prior Publication Data
US 2015/0343116 A1    Dec. 3, 2015

Related U.S. Application Data

(60) Provisional application No. 61/751,926, filed on Jan. 13, 2013.

(51) Int. Cl.
| | |
|---|---|
| *A61L 27/44* | (2006.01) |
| *A61L 27/34* | (2006.01) |
| *A61L 27/50* | (2006.01) |
| *A61L 27/36* | (2006.01) |

(52) U.S. Cl.
CPC ............... *A61L 27/44* (2013.01); *A61L 27/34* (2013.01); *A61L 27/3608* (2013.01); *A61L 27/50* (2013.01); *A61L 27/502* (2013.01); *A61L 2430/02* (2013.01)

(58) Field of Classification Search
CPC .. A61L 2430/02; A61L 27/34; A61L 27/3608; A61L 27/44; A61L 27/50
See application file for complete search history.

(56) References Cited

U.S. PATENT DOCUMENTS

| | | | |
|---|---|---|---|
| 8,859,007 B2 * | 10/2014 | Carter | A61L 27/50 106/637 |
| 2002/0106394 A1 * | 8/2002 | Tucker | A61L 2/0011 424/423 |
| 2009/0130173 A1 | 5/2009 | Behnam et al. | |
| 2010/0036503 A1 | 2/2010 | Chen et al. | |
| 2011/0195052 A1 | 8/2011 | Behnam et al. | |
| 2012/0082704 A1 * | 4/2012 | Phillips | A61K 9/0026 424/400 |
| 2012/0258178 A1 | 10/2012 | Benham et al. | |

OTHER PUBLICATIONS

International Search Report and Written Opinion mailed on Apr. 25, 2014 for corresponding International Application No. PCT/US14/11359, 7pp.

* cited by examiner

*Primary Examiner* — Michael B Pallay
(74) *Attorney, Agent, or Firm* — Lewis Roca Rothgerber Christie LLP

(57) ABSTRACT

An encapsulated three-dimensional (3-D) bone matrix composition for inducing bone growth includes a 3-D bone matrix, an oxygen carrier incorporated into the 3-D bone matrix, and an encapsulation material which encapsulates the 3-D bone matrix incorporated with the oxygen carrier. Methods are disclosed for preparing an encapsulated 3-D bone matrix that can be maintained in packaging.

6 Claims, No Drawings

OXYGENATED THREE-DIMENSIONAL MATRIX FOR BONE GROWTH

CROSS-REFERENCE TO RELATED APPLICATION

This application is a National Phase Patent Application and claims the priority of International Application Number PCT/US2014/011359, filed on Jan. 13, 2014, which claims priority of U.S. Provisional Application No. 61/751,926, filed on Jan. 13, 2013. The disclosures of which are hereby incorporated by reference.

Improving the processing and administration of an oxygenated bone matrix composition will improve the osteogenesis, osteoconduction, and osteoinduction capabilities in bone grafting to advance the state of the art in bone repair. For three-dimensional (3-D) demineralized bone matrix (DBM), preserving the oxygenated matrix is challenging given the hydrophobic nature of the oxygen carrier material as well as the 3-D structure of the matrix. For example, perfluorocarbons (PFCs) are oxygen carriers, and are extremely hydrophobic viscous liquids which render making a formulation suitable for implantation into patients using PFCs very challenging. Accordingly, a need exists for an oxygenated 3-D bone matrix for bone growth that can be maintained in packaging from the time of manufacturing until its use.

SUMMARY

In some embodiments, an encapsulated three-dimensional (3-D) matrix composition for inducing bone growth includes a 3-D matrix, an oxygen carrier incorporated into the 3-D bone matrix, and an encapsulation material that encapsulates the 3-D bone matrix incorporated with the oxygen carrier.

In some embodiments, a method of making an encapsulated oxygenated three-dimensional (3-D) matrix includes incorporating an oxygen carrier into a 3-D bone matrix to form an oxygenated 3-D bone matrix, and incorporating an encapsulation material into the oxygenated 3-D bone matrix to form an encapsulated oxygenated 3-D bone matrix.

DETAILED DESCRIPTION

The present disclosure describes an oxygenated 3-D bone matrix for inducing bone growth that retains the incorporated oxygen carrier and is capable of being maintained in a package. Maintaining and preserving the incorporation of an oxygen carrier in a 3-D bone matrix is difficult because of the matrix structure that is not conducive to mixing and the hydrophobicity of oxygen carriers. For example, in a demineralized bone matrix (DBM) that is incorporated with a perfluorocarbon (PFC), the PFC is hydrophobic and the DBM is hydrophilic. As disclosed herein, a 3-D bone matrix is incorporated with an oxygen carrier and the oxygenated 3-D bone matrix is then encapsulated for packaging and later use.

It has previously been demonstrated that PFC's can be applied to various matrices including DBM and enhance cellular activity, as described in U.S. patent application Ser. No. 13/740,244, the entire contents of which are herein incorporated by reference.

As used herein the term demineralizing refers to demineralization of bone. The decrease in the amount of calcium in the bone determines the amount of demineralization. That is, completely demineralized bone has no calcium, or only trace amounts of calcium. In some embodiments completely demineralized bone has no more than 10% calcium.

In some embodiments, a 3-D bone matrix includes an oxygen carrier incorporated within a stable formulation. In some embodiments, the oxygen carrier is a PFC. A stable formation includes encapsulation which retains the incorporated PFC and decreases elution of the PFC from the matrix. In some embodiments, the oxygenated 3D matrix is stable while packaged.

Non-limiting examples of 3-D matrices include: a demineralized cancellous DBM sponge, a DBM fiber matrix, and non-demineralized cancellous strips. Non-limiting examples of demineralized cancellous DBM sponge are disclosed in U.S. Provisional Application No. 61/877,825, Appendix I, the entire contents of which are herein incorporated by reference. Non-limiting examples of a DBM fiber matrix include Grafton® Flex, Grafton® Matrix, Grafton® Matrix Strips, and those disclosed in U.S. Provisional Application No. 61/864,499, the entire contents of which are herein incorporated by reference. In some embodiments, the 3-D bone matrix is a demineralized cancellous DBM sponge.

In some embodiments, the oxygen carrier is a perfluorocarbon (PFC). Non-limiting examples of PFCs include perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecane, perfluorotripropylamine, perfluorotrimethylcyclohexane, perfluoromethyladamantane, perfluorodimethyladamantane, perfluoromethyldecaline, perfluorofluorene, diphenyldimethylsiloxane, hydrogen-rich monohydroperfluorooctane, alumina-treated perfluorooctane, mixtures thereof, or any suitable oxygen carrier.

The choice of material used for encapsulation influences the performance of the 3-D bone matrix. Encapsulation material is characterized by the following: i) it retains the oxygen carrier within the 3-D bone matrix, ii) it does not interfere with the rehydration of the 3-D bone matrix, and/or iii) it is capable of being mixed with bone marrow aspirate. As such, encapsulation materials are hygroscopic, rehydrate rapidly, and rapidly dissolve or remodel.

In some embodiments, a porous 3-D bone matrix is soaked in an oxygen carrier (e.g., a PFC), and the oxygen-soaked 3-D bone matrix is then immersed in a collagen-derived material (e.g., gelatin) to form an encapsulated oxygenated 3-D bone matrix. Additional encapsulation materials include glycerols, lecithins, polyoxamers, phospholipids, and other suitable materials having the identified characteristics.

In some embodiments, the oxygen carrier is combined with other dispersing agents to form an emulsion, gel or admixture, and this mixture is then incorporated into the 3-D bone matrix. Non-limiting examples of dispersing agents include glycerols, phospholipids, lecithins, surfactants, and polyoxymers.

In some embodiments, DBM powder is combined with an oxygen carrier to form an oxygenated DBM slurry mixture as described in U.S. application Ser. No. 13/740,244, the entire contents of which are herein incorporated by reference. Specifically a PFC as disclosed herein is mixed with DBM (powder or chips) to form a DBM/PFC mixture. In some embodiments, the amount of PFC in the PFC/DBM mixture is in the range of about 32-48 weight %. Sterile saline is then added to provide a slurry with the handling characteristics of wet sand. This oxygenated DBM slurry mixture is then incorporated into the 3-D bone matrix. The addition of DBM powder enhances the osteoinductive potential of the 3-D bone matrix.

In some embodiments, the process for oxygenating and encapsulating the 3-D bone matrix includes soaking the 3-D bone matrix in a plasticizing agent (also known as a swelling agent) until the matrix is fully saturated. The saturated 3-D bone matrix it is then lyophilized (e.g., dehydration) to remove any water, leaving behind the plasticizing agent that keeps the matrix pliable. In some embodiments the plasticizing agent is mixed with water to help facilitate incorporation of the plasticizer into the matrix. Non-limiting examples of plasticizing agents include phospholipids, liquid polyhydroxyl compounds and liquid polyhydroxyl compound derivatives. The polyhydroxyl compounds and derivatives of this type include those which in the pure or concentrated state and at ambient temperature are normally solid or semi-solid but are soluble in a suitable solvent, e.g., water, physiological saline, ethanol, glycerol, glucose, propylene glycol, polyethylene glycol of from 200-1000 molecular weight, etc., or mixtures thereof, to provide a liquid composition.

In particular, useful polyhydroxyl swelling agents possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives thereof. Specific polyhydroxyl compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, trehalose, carrageenan, agar, alginic acid, guar gum, gum tragacanth, locust bean gum, gum arabic, xanthan gum, amylose, mixtures and copolymers thereof.

After saturation and lyophilization, an oxygen carrier is then added to the saturated and lyophilized matrix. The oxygenated bone matrix is then placed into a collagen solution for encapsulation of the oxygenated matrix. This encapsulated and oxygenated 3-D bone matrix is placed into standard packaging formats without the need for special handling.

The following Examples are presented for illustrative purposes only, and do not limit the scope or content of the present application.

Example 1. Incorporation of PFTBM into a 3-D DBM Matrix

A piece of demineralized allograft cancellous bone sponge (DCS) (OsteoSponge®, Bacterin) weighing 0.3 grams was placed into a vial containing PFTBM (Sigma Aldrich), and agitated for 5 minutes. The DCS was removed from the vial and the free PFTBM allowed to drain. The weight was 1.36 grams. The sample was then blotted using non-linting paper and a final weight of 0.85 grams recorded. From the dimensions of the sponge it could be calculated that the PFTBM concentration was 0.92 g/cm$^3$. The impregnated DCS was then dipped into a second solution of Pluronic F-68 in N-methyl-2-pyrrolidone (NMP) to encapsulate the construct, trapping the PFC inside.

Example 2. Incorporation of PFTBM into a 3-D DBM Matrix

A piece of demineralized allograft cancellous bone sponge (DCS) (OsteoSponge®, Bacterin) weighing 0.26 grams was placed into a vial containing PFTBM and agitated for 5 minutes. The DCS was removed from the vial and the free PFTBM allowed to drain. The weight was 1.05 grams. The sample was then blotted using non-linting paper and a final weight of 0.87 grams recorded. From the dimensions of the sponge it could be calculated that the PFTBM concentration was 1.04 g/cm$^3$. The impregnated DCS was then dipped into a solution of lecithin in water to encapsulate the construct, trapping the PFC inside. The sample was then dried in a vacuum oven.

Example 3. Incorporation of PFTBM into a 3-D DBM Matrix

A piece of demineralized allograft cancellous bone sponge (DCS) (OsteoSponge®, Bacterin) weighing 0.14 grams was placed into a vial containing PFTBM and agitated for 5 minutes. The DCS was removed from the vial and the free PFTBM allowed to drain. The weight was 0.57 grams. The sample was then blotted using non-linting paper and a final weight of 0.37 grams recorded. From the dimensions of the sponge it could be calculated that the PFTBM concentration was 0.5 g/cm$^3$. The impregnated DCS was then dipped into a second solution of gelatin to encapsulate the construct, trapping the PFC inside.

APPENDIX I     US Prov. Appln 61/877,825

72950/T668

COMPOSITIONS OF AND METHODS FOR CANCELLOUS BONE MATRIX

CROSS-REFERENCE TO RELATED APPLICATION(S)

[0001] This application is related to U.S. Provisional Application No. 61/814,197, titled "Bone Graft and Method for Making (Cancellous/DBM), filed April 19, 2013.

BACKGROUND

[0002] Bone grafts are commonly required to treat defects in the skeletal system caused by injury, disease or other defects. Defects often require such grafts to maintain space and provide a matrix for healing. The properties of the graft must support the healing response that is due to various mechanisms of bone healing known as osteoconduction, osteoinduction and osteogenesis. Osteoconduction is the ability of the graft to act as a matrix to support bone formation imitated by bone forming cells. Osteoinduction is a result of bone growth factors that stimulate differentiation of local cells to become bone forming cells, i.e. osteoblasts. Bone morphogenic proteins (BMP's) that are naturally occurring in bone, or that may be produced by recombinant gene technologies are responsible for osteoinduction. Osteogenesis refers to the ability of cells to directly form bone at the site of implantation due to normal physiological processes. These cells may be either resident at the graft site or transplanted to the site by autogenous bone, bone marrow aspirate, and/or implanted cells. There is a need for bone grafts to have osteoconductive, osteogenic and osteoinductive properties to support bone formation and healing.

[0003] As used herein, *cortical bone* is dense bone that forms the shafts and surface layers of metaphyseal regions as well as the surface layer of flat bones, e.g. iliac crest. Cortical bone is dense with ≤10% porosity. The porosity of cortical bone may be formed by vascular channels (Volksmann's and Haversian canals), lacunae where bone cells within the matrix reside, and/or canaliculi which provide a channel for nutritional transport and cell to cell communication. As APPENDIX I    US Prov. Appln 61/877,825

72950/T668 used herein, *cancellous bone*, also known as 'spongiosa,' has a macroporous architecture resembling a sponge. Cancellous bone is much less dense than cortical bone with the void space of cancellous bone being approximately 50% or greater. The porosity of cancellous bone depends on several factors, including anatomical location, i.e., cancellous bone is more dense just below joint surfaces and becomes more porous further from the joint. Other factors including metabolic state of the individual also influence porosity of cancellous bone.

[0004] The term *demineralized bone* is used to describe a process where acid (e.g. 0.6N HCl) is used to remove mineral from bone. As used herein the term *demineralizing* refers to a process where acid is used to remove mineral from bone. The decrease in the amount of calcium in the bone determines the amount of demineralization. That is, completely demineralized bone has no calcium, or only trace amounts of calcium. In some embodiments completely demineralized bone has no more than 10% calcium. Any suitable acid or chelating may be used. An example of a suitable acid is 0.6N HCl. An example of a suitable chelating agent is ethylenediamine tetraacetic acid (EDTA). By reducing the pH to the level where bone mineral becomes soluble, the mineral component can be leached from the bone, leaving behind primarily type I collagen, as well as other components of bone, including growth factors that can influence bone healing by a process known as osteoinduction.

[0005] Both cortical bone and cancellous bone may be demineralized. Both demineralized cortical bone and demineralized cancellous bone may be in the form of a powder or particulate or segments where the native three-dimensional architecture is maintained. As used herein, *powder* and *particulate* are used to describe cortical and/or cancellous bone that has been ground, pulverized, or shredded, into granules, a powder, or elongate particles or other shapes of various sizes.

[0006] As used herein, cancellous bone that maintains its natural three-dimensional architecture and porosity is referred to as *cancellous bone matrix* or *demineralized cancellous bone*

APPENDIX I    US Prov. Appln 61/877,825

72950/T668

*matrix.* Cancellous bone that has been ground, etc. is referred to as cancellous powder or cancellous particulate. Demineralized cancellous bone that has been ground, etc., is also referred to as DBM (Demineralized Bone Matrix) or DBM powder or Demineralized Cancellous Powder.

[0007]    As used herein, demineralized cortical bone is referred to as demineralized bone matrix (DBM), DBM powder or demineralized cortical powder.

SUMMARY

[0008]    Some embodiments of the present invention are directed to a bone repair composition, including a cancellous bone matrix, and bone particles.

[0009]    Some embodiments of the present invention are directed to methods of making a bone repair composition including hydrating a dehydrated cancellous bone matrix and loading cortical bone particles into the cancellous bone matrix. In some embodiments, the cortical bone particles are suspended in a hypertonic solution and loaded into the cancellous bone matrix in this hypertonic solution. In some embodiments, water is removed from the loaded cancellous bone matrix and then a hypotonic solution is loaded into the particle-loaded matrix to swell the cortical bone particles, thereby effectively securing the cortical bone particles within the cancellous bone matrix.

[0010]    In one embodiment of the present invention the cancellous bone matrix is impregnated with demineralized fibers configured to bind to the cancellous bone matrix. The demineralized fibers have the advantage that they can be more tightly bound.

[0011]    In one embodiment of the present invention the cancellous bone matrix is impregnated with a combination of crushed cortical bone and cancellous bone in the form of powder. The use of both cortical and cancellous bone utilizes more of the donated tissue APPENDIX I    US Prov. Appln 61/877,825

72950/T668

[0012] In one embodiment of the present invention a coating is applied around the cancellous bone matrix to contain the DBM powder, so that the DBM powder is not directly bound but is "contained". This containment by means of a coating has the advantage of increasing the total content of DBM powder in the cancellous bone matrix because otherwise any non-bound DBM powder would fall out. Various biocompatible water soluble or biodegradable materials may be used, such as, but not limited to gelatin, collagen, polyvinyl alcohol, hyaluronic acid and other water soluble polymers.

[0013] In some embodiments the cancellous bone matrix may be completely filled with demineralized cortical powder/particulate and/or demineralized cancellous powder/particulate. In other embodiments, areas of the cancellous matrix are unfilled in order to facilitate the addition of further components intraoperatively. These additional components may include bone marrow aspirate or morcellized bone from the patient, cells, growth factors or other exogenous factors. By not fully impregnating the cancellous matrix, usage of the powder/particulate component is reduced, thereby reducing waste and cost and effectively using scarce donated tissue. For example if a 1 cm x 1 cm x 1 cm cancellous bone matrix cube is filled with DBM powder and the surrounding 1 mm of space on all six sides of the cube is evacuated of DBM powder by shaking the powder out, by other means, then approximately 75% of the cube at the innermost extremes is impregnated, while approximately 1 mm on the outside remains available for facilitating infusion of bone marrow aspirate or other preferred materials to enhance bone growth. The cancellous bone matrix cube is often compressed before insertion into a bone void and allowed to refill into the available space. The surfaces of bone in contact with the inserted cube are rich in osteogenic and osteoinductive components. These would be in contact with the cube and easily infuse into the outer areas that are void of DBM powder. As such, these outer regions of the cancellous bone matrix cube have a high osteogenic potential without the presence of the DBM powder.

APPENDIX I     US Prov. Appln 61/877,825

72950/T668

[0014] While it is beneficial to use less DBM powder – saving cost and donated tissue-- the availability of "open" areas, especially near the periphery of the cancellous bone matrix increases the ability to absorb these components and allows for comparable or improved results.

[0015] In some embodiments of the present invention, a kit includes the cancellous bone matrix and bone powder. At the time of the procedure the bone particles are suspended in saline or bone marrow aspirate and infused into the cancellous bone matrix.

BRIEF DESCRIPTION OF THE DRAWINGS

[0016]

[0017]

[0018]

[0019]

DETAILED DESCRIPTION

Figures 1A, 1B:
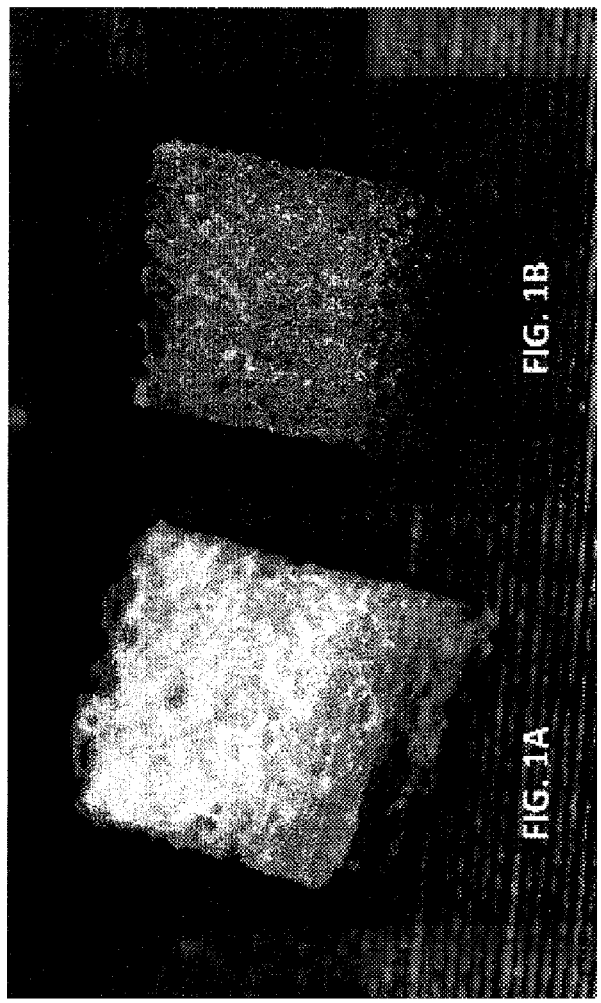
FIG. 1A is a photograph of demineralized cancellous bone with demineralized cortical powder (DCP), according to embodiments of the present invention.
FIG. 1B is a photograph of demineralized cancellous bone without DCP.
Figures 2A, 2B:
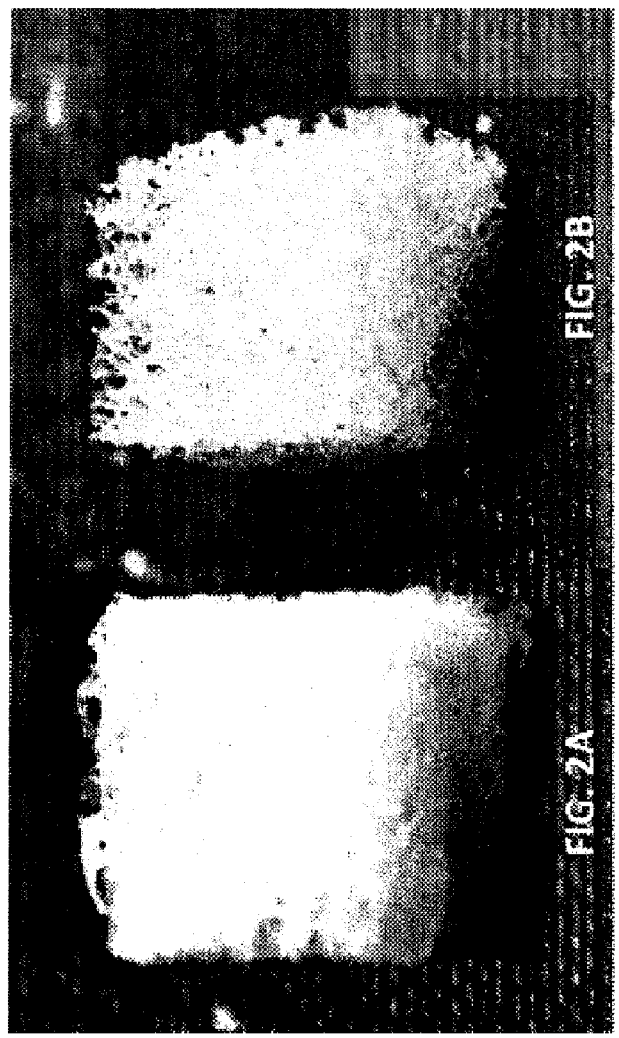
FIG. 2A is a photograph showing a closer view of the demineralized cancellous bone with DCP of FIG. 1A.
FIG. 2B is a photograph showing a closer view of the demineralized cancellous bone without DCP of FIG. 1B.

[0020] In some embodiments of the present invention, a bone repair composition for treating defects of bones includes a mineralized or demineralized cancellous bone matrix and demineralized cortical bone, demineralized cancellous bone, or demineralized cortical and cancellous bone all derived from allogeneic (human) or xenogeneic (animal) sources. The combination of cancellous bone matrix and demineralized cortical and /or demineralized cancellous particulate bone provides APPENDIX I    US Prov. Appln 61/877,825

72950/T668 a product that has the advantages of cancellous bone matrix having a higher overall density of bone. Thus the combination includes a higher proportion of osteoinductive proteins. The use of demineralized cortical bone powder together with cancellous bone yields a product incorporating the advantages found in each of cancellous bone. That is, cancellous bone has an interconnected, highly porous structure that provides an excellent matrix architecture for the formation of new bone, i.e., it is highly osteoconductive. To complement the cancellous bone cancellous bone matrix, the demineralized bone particles that includes only cortical bone, or a high proportion of cortical bone, is highly osteoinductive. The osteoinductive proteins (e.g., bone morphogenic proteins (BMPs)) that are 'unmasked' by the removal of the hydroxyapatite mineral component are capable of guiding the differentiation of uncommitted cells at the site of implant into bone forming cells. Containment of these osteoinductive agents within a cancellous bone matrix that is highly osteoconductive allows for efficacious bone formation. The combination of these properties provides for a bone repair composition having improved utility for bone growth.

[0021] In some embodiments, the present repair composition of the present invention may include additional additives selected to enhance the handling properties and bone healing performance of the constructs. Selected additives are added to the bone repair composition to improve physical and/or physiological effects. In some embodiments, an additive is selected to hydrate the cancellous bone matrix to maintain "sponginess" in the absence of water. An example of a hydrating additive includes glycerol. In some embodiments, an additive is selected to improve the bone growth effect or other physiological effects of the bone repair composition. For example, a selected additive may include perfluorocarbons (PFCs) and/or other oxygen-generating compounds in order to enhance the ability of the cells within the cancellous bone matrix to form bone. In other examples, selected additives to promote bone growth and healing include growth factors, cells with bone forming potential and/or immune modulatory potential e.g. mesenchymal stem cells MSCs, or bone marrow cells, antibiotics, anti-neoplastic agents, oxygenating materials, APPENDIX I    US Prov. Appln 61/877,825

72950/T668 and combinations thereof. In some embodiments, an additive is selected to inhibit microbial growth. For example, a selected additive may be gentamicin. Non-limiting examples of additives to enhance bone growth include growth factors such as bone morphogenetic proteins (BMPs), including BMP-1, BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, and BMP-18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-$\beta$s), including TGF-$\beta$-1, TGF-$\beta$-2, and TGF-$\beta$-3, and inhibitors for tumor necrosis factor (e.g., anti-TNF-$\alpha$). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, the entire contents of which is incorporated herein by reference. The polynucleotides encoding the same may also be administered as gene therapy agents. The preferred bioactive substances are the recombinant human bone morphogenetic proteins (rhBMPs) because they are available in relatively unlimited supply and do not transmit infectious diseases. In some embodiments, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al., the entire contents of all of which are herein incorporated by reference.

APPENDIX I    US Prov. Appln 61/877,825

72950/T668

[0022]    In some embodiments, selected additives include those that improve physical handling properties, e.g., plasticizers, binders, adhesives, wetting agents, and surfactants.

[0023]    In some embodiments, a biocompatible material is included to enhance the osteogenic properties of the bone implant. The addition and selection of at least one biocompatible material may depend on the size of the bone graft site and the location of the site. A broad range of biocompatible materials are available, including: collagen and insoluble collagen derivatives, hydroxyapatite, tricalcium phosphate, and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin; amino acids, magainins, peptides, vitamins, inorganic elements, cofactors for protein synthesis; hormones; endocrine tissue or tissue fragments; synthesizers; enzymes such as collagenase, peptidases, and oxidases; polymer cell scaffolds with parenchymal cells; surface cell antigen eliminators; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; nucleic acids; and, bioerodable polymers such as those disclosed in U.S. Pat. Nos. 4,764,364 and 4,765,973 and European Patent Application 168,277. The amounts of such optionally added substances can vary widely with optimum levels being readily determined by those having ordinary skill in the art.

APPENDIX I    US Prov. Appln 61/877,825

72950/T668

[0024] In one embodiment of the present invention the cancellous bone matrix is impregnated with demineralized fibers configured to be contained within the cancellous bone matrix. The demineralized fibers have the advantage that they can be more easily contained within the cancellous bone matrix. That is, the demineralized cortical and/or cancellous bone fibers may have more than one point of contact within a pore or pores of the cancellous bone matrix.. The demineralized fibers have the advantage that most of the fibers provided to the cancellous bone matrix are able to be contained, thereby providing demineralized bone powder/particulate more consistently to the cancellous bone matrix for increased reproducibility and quality of the cancellous bone and demineralized bone particulate/powder composition.

[0025] In one embodiment of the present invention, the cancellous bone matrix is impregnated with a combination of crushed cortical bone and cancellous bone in the form of powder. This combination of cortical bone and cancellous bone has the advantage of utilizing more donated tissue.

[0026] In one embodiment of the present invention, a coating is applied around the cancellous cube to contain the DBM powder, so that it is "contained". This coating may allow an increased content of DBM powder by preventing any non-bound DBM powder from falling out. Various water-soluble or degradable materials may be used, such as, but not limited to gelatin, collagen, polyvinyl alcohol, polyacrylic acid, polyacrylamide, polyethylene glycol, polyethylene-propylene glycol, dextran, xanthum gum, carrageenan, carboxymethyl cellulose, hyaluronic acid.

[0027] In some embodiments the cancellous bone matrix may be completely filled with demineralized cortical and/or cancellous powder/particulate, thereby having uniformly dispersed powder/particulate. In other embodiments, some areas of the cancellous bone matrix are left unfilled to facilitate addition of further components intraoperatively, and thereby having non-uniformly dispersed powder/particulate. These may include bone marrow aspirate or morcellized bone from the patient, cells, growth factors or other exogenous factors. By not fully impregnating APPENDIX I   US Prov. Appln 61/877,825

72950/T668 the cancellous bone matrix, the amount of the bone powder/particulate component is reduced which avoids waste and saves cost and donated tissue. For example if a 1 cm x 1 cm x 1cm cancellous bone matrix cube is filled with DBM powder and then the surrounding 1 mm of space on all six sides of the cube is evacuated of DBM powder by shaking the powder out, by other means, then approximately 75% of the cube at the innermost extremes is impregnated, while just 1 mm on the outside remains available for facilitating infusion of bone marrow aspirate or other preferred materials to enhance bone growth. In some embodiments, the cancellous bone matrix cube is compressed before insertion into a bone void and allowed to refill into the available space. The surfaces of the patient's bone in contact with the inserted cube are rich in osteogenic and osteoinductive components. These would be in contact with the cube and easily infuse into the outer areas that are specifically voided of DBM powder. As such, these outer regions have a high osteogenic potential without the presence of the DBM powder.

[0028] While it is a benefit in the utilization of less DBM powder – saving cost and donated tissue, the availability of "open" areas, especially near the periphery of the cancellous bone matrix increases the ability to absorb these components and allows for comparable or improved results.

[0029] Moreover, the bone repair compositions of the present invention have at least the following characteristics: 1) easy to handle during the surgical procedure; 2) enhanced bone forming capability due the DBM powder, 3) enhanced bone forming capability due to the oxygen transport and selected additives also disclosed herein; and 3) biocompatible and easily mixed with ancillary constituents commonly used during grafting procedures, e.g., autograft bone and bone marrow aspirate.

[0030] In some embodiments of the present invention, the bone graft composition includes an excipient to facilitate the loading and retention of particulates into the cancellous bone matrix. In some embodiments, the particulates include demineralized cortical bone powder/particulate, demineralized cancellous bone powder/particulate or combinations thereof. With suspension of APPENDIX I    US Prov. Appln 61/877,825

72950/T668 demineralized bone powder/particulate in an excipient, the cortical or mixture of cortical and cancellous bone powder can be effectively incorporated into the cancellous bone matrix. In some embodiments, an excipient for loading the particulates into the cancellous bone matrix is an excipient solution. Non-limiting examples of excipient solutions for loading and retention of particulates include glycerol, alcohols, hypertonic solutions, wetting agents, and combinations thereof.

[0031] Of the possible excipient solutions, hypertonic solutions cause the cortical bone particles to shrink, which may be desired for loading the particles into the cancellous bone matrix. In some embodiments, after loading of the smaller particles, the cancellous bone matrix is then dehydrated to remove the water from the hypertonic solution. The cortical bone particles in the cancellous bone matrix are then enlarged (i.e. swollen) by the addition of a hypotonic or isotonic solution that acts as a 'swelling agent.' In this way, the shrunken particles that have already been introduced into the pores of the cancellous bone matrix are then swollen, thereby effectively "locking" or securing the particles into the pores of the matrix. Non-limiting examples of swelling agents include glycerol, lecithin and wetting agents (e.g., surfactants).

[0032] In particular, useful polyhydroxy swelling agents possess from 2 up to 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives thereof. Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamnose, inositol, fructose, galactose, glucose, mannose, sorbose, sucrose, maltose, lactose, maltitol, lactitol, stachyose, maltopentaose, cyclomaltohexaose, trehalose, carrageenan, APPENDIX I    US Prov. Appln 61/877,825

72950/T668 agar, alginic acid, guar gum, gum tragacanth, locust bean gum, gum arabic, xanthan gum, amylose, mixtures and copolymers thereof.

[0033] In some embodiments, demineralized cortical and/or cancellous bone powder/particulate is suspended in a glycerol and water solution, and this particulate suspension is then loaded into a demineralized cancellous bone matrix graft. The vapor point of glycerol is much higher than water, so the water is easily removed, leaving behind the glycerol to maintain the spongy character of the demineralized cancellous matrix. Glycerol is also extremely hydroscopic, such that water, saline, blood, bone marrow aspirate or similar aqueous liquids are readily imbibed, allowing for excellent handling characteristics during surgery. As such, once the particulate has been introduced into the cancellous bone matrix using an excipient, the particulate may then be encapsulated within the cancellous bone matrix by removing the swelling/shrinking agents. This approach is an example of incorporating the particles into the porous three-dimensional structure of the cancellous bone matrix, and subsequently holding them in place such that the particles are not removed during handling prior to or during surgical procedures. In other embodiments, other agents may be used to hold the particles in place by means of electrostatic charge and/or surface attraction.

[0034] The size of the cancellous graft can range from a few millimeters to several centimeters depending on the intended procedure. Anatomical constraints limit the upper range of sizes. Cancellous bone from allogeneic sources (human donors) is limited by the size of the femur and tibial metaphyses, whereas bone from other species such as bovine bone has larger potential sizes. The graft may be used in the form of a monolithic implant or may be granules formed from the enhanced cancellous bone matrix.

[0035] In some embodiments the size of demineralized bone particles is matched to the size of the cancellous matrix pores. Demineralized cortical and/or demineralized cancellous bone particles are produced by conventional means and then size selected and classified by sieving. The APPENDIX I    US Prov. Appln 61/877,825

72950/T668 cancellous bone matrix pore size is estimated by measuring with calipers or from a microscope image and then particles selected to fit snuggly into the pores. The bone particles are then impregnated or dispersed into the cancellous matrix by various means described elsewhere in this disclosure.

[0036] In some embodiments particles of demineralized bone are designed such that once impregnated into the pores of the matrix, they are not easily dislodged. Particles with a high surface area ratio such as discs and elongate fibers have a greater contact surface within the cancellous matrix pores resulting in them being more tightly bound and less prone to dislodgement.

[0037] In other embodiments, once demineralized bone particles are impregnated into a cancellous bone matrix the construct is impregnated with a solution of a polymer to enhance the binding of the bone particulates to the cancellous bone matrix. Suitable materials include trehalose, lecithin and collagen that has been treated to have a sticky consistency, thus binding the particles within the matrix. Such a collagen preparation can be produced by heating bone collagen in an acid solution, as is described by O'Leary and Prewett in US 5,236,633, the entire contents of which are herein incorporated by reference.

[0038] In some embodiments the demineralized particles are impregnated or dispersed into the central regions of the cancellous bone matrix, but not in the periphery of the cancellous bone matrix. Various means described elsewhere herein, may be used to adhere the particles. This allows for areas within the cancellous bone matrix to be available for incorporation of bone marrow aspirate, morcellized bone from the patient or other materials into the pores of the matrix without dislodging the impregnated particles and has advantages in that less particulate material is required resulting in cost savings and avoiding wasting donor tissue.

[0039] In some embodiments the demineralized particles are injected into the central regions of the cancellous bone matrix using a syringe and needle type of approach. This allows for controlled placement of the particulate within the cancellous matrix. This method may also be used APPENDIX I    US Prov. Appln 61/877,825

72950/T668 intraoperatively where the particulate is mixed with bone marrow aspirate and then infused into the graft at the time of use.

[0040] In various embodiments, after impregnating cancellous bone matrix with demineralized particles, a heating step is performed where the construct is heated to an elevated temperature between about 40°C and about 70°C degrees while in a hydrated state for a period of about 30 minutes up to about 24 hours. These conditions result in alterations in the collagen within bone that cause it to adhere to other particles and the surface of the matrix.

[0041] In one aspect of the invention the cancellous matrix and demineralized bone powder are provided in a kit. At the time of the procedure the bone particles are suspended in a liquid and infused into the matrix.

[0042] The bone particles may be suspended in saline, bone marrow aspirate or a perfluorocarbon. Suitable perfluorocarbons include perfluorodecalin, perfluorohexane, perfluorotributylamine, or perfluoroperhydrophenanthrene. Perfluorocarbons have a high oxygen solubility and act as reservoirs of oxygen. The use of perfluorocarbons has been shown to be advantageous to bone repair.

[0043] In some embodiments, the kit includes separate syringes to contain the cancellous matrix and bone particles and may be connected to allow the suspension to be infused into the matrix. Furthermore, the syringe containing the matrix imparts a reduced pressure, effected by pulling the plunger back on that syringe or on a conjoined syringe.

[0044] In some embodiments the kit includes syringe and needles for harvesting of the patient's bone marrow.

[0045] The following Examples of the bone repair composition are presented for illustrative purposes only, and do not limit the scope or content of the present application.

APPENDIX I     US Prov. Appln 61/877,825

72950/T668

EXAMPLES

[0046] Example 1. Rehydration of Cancellous Bone Matrix. A demineralized and dehydrated (freeze-dried) cancellous bone matrix cube ("cube") approximately 1 cm$^3$ in size was supplied by Bacterin International Holdings, Inc. The cube was placed into a solution of 35% glycerol in water. The cube was soaked in the glycerol solution for approximately one hour, at which point the cube was rehydrated --i.e., it was compressible and spongy, as opposed to the stiffness and brittleness of the bone cube before rehydration. The rehydrated cube was removed from the glycerol solution, blotted dry and placed into a vacuum oven to remove any additional moisture.

[0047] Example 2. Influence of 70% ethanol and glycerol on volume of demineralized cortical powder (DCP). DCP was placed into a vial filling to the 4cc mark. 70% ethanol was then added to the 10cc mark. After incubating for 1 hour at room temperature, the vial was centrifuged at 500rpm for 30 seconds. The DCP was at the 5cc mark. The fluid was decanted and replaced by water, then centrifuged as above. This was repeated twice. The DCP was fully rehydrated and now the powder level was at 5.6cc in the vial demonstrating approximately 10% swelling by use of the 70% ethanol. The water was then decanted and 2cc of glycerol added, then additional water to the 10cc mark. After shaking to mix and centrifuging as above, the powder level was now at 6cc. This demonstrated the DCP had swollen approximately 20% compared to the 70% ethanol solution and 10% compared to water. This experiment demonstrates feasibility to cause swelling of DCP by controlling the solution it is rehydrated in.

[0048] Example 3. Loading of DCP/Glycerol into Cancellous Bone Matrix. Demineralized cortical powder (DCP) was prepared as follows: 1.21 grams of DCP from AlloSource was placed into a vial and 6.02 gm of a 50% glycerol/water solution was added. The mixture was shaken and allowed to incubate at room temperature in a sealed vial for 24 hours. Again, swelling was noted as in Example 2 above. This mixture was then placed into a syringe with its end removed such that it was a cylinder with a plunger, and the mixture of DCP was forced into the cube by placing the tip APPENDIX I    US Prov. Appln 61/977,825

72950/T668 onto the cube and compressing the cube flat. As the mixture was expelled onto the cube, the downward force on the cube was slowly reduced, to allow it to return to its normal shape, with the DCP loaded inside the pore spaces.

[0049] Example 4. Loading of DCP/Ethanol into Cancellous Sponge A demineralized and dehydrated cancellous bone matrix cube (Bacterin, *supra*) was placed in a 70% ethanol and water solution without a glycerol rehydration step as described in Example 1. DCP was suspended in a 70% ethanol solution. The DCP suspension did not result in rehydration and swelling of the powder, but instead the DCP particle size remained small. The DCP solution was then introduced into the cube using the same syringe as described above, but injecting it by forcing it into the matrix of the uncompressed cube. The resulting construct was then placed into a vacuum oven to remove the water and ethanol, leaving the dried DCP within the matrix. The result was a demineralized cancellous bone matrix cube (DCC) loaded with DCP in the internal architecture.

[0050] Example 5. Glycerol Rehydration of DCP/Ethanol-Loaded Cancellous Bone Matrix. The DCP-loaded cancellous bone matrix from Example 3 was placed into a 35% glycerol solution followed by rehydration for 1 hour, resulting in softening of the cancellous bone matrix and swelling of the loaded DCP therein. The glycerol solution induced swelling and enlargement of the DCP particles, and secured the DCP in place within the cancellous bone matrix. This glycerol and DCP-loaded cancellous bone matrix was placed into a vacuum oven to remove the water, leaving behind the glycerol which maintained hydration of the cancellous bone matrix such that it was compressible. The glycerol further provided 'stickiness' which helped retain the DCP in the cancellous bone matrix.

[0051] Example 6. Lecithin Rehydration of DCP/Ethanol-Loaded Cancellous Sponge. The DCP-loaded cancellous sponge from Example 3 was placed into a 10% lecithin solution followed by rehydration for 1 hour, resulting in softening of the cube and swelling of the loaded DCP therein. The lecithin solution induced swelling and enlargement of the DCP particles, and secured APPENDIX I    US Prov. Appln 61/877,825

72950/T668 the DCP in place within the sponge matrix. This lecithin and DCP-loaded sponge cube was placed into a vacuum oven to remove the water, leaving behind the lecithin which maintained hydration of the construct such that it was compressible. The lecithin further provided 'stickiness' which helped retain the DCP in the sponge matrix. This example demonstrates that swelling agents other than glycerol are effective at increasing the volume of DCP.

[0052] Example 7. Sucrose/Glycerol Rehydration of DCP/Ethanol-Loaded Cancellous Sponge. The DCP-loaded cancellous sponge from Example 3 was placed into a 10% sucrose and 25% glycerol in water solution for 1 hour. This sucrose/glycerol and DCP-loaded sponge cube was then placed into a vacuum oven to remove the water, leaving behind the sucrose and glycerol. The sucrose appeared to provide additional binding and "stickiness" to retain and "lock" the DCP particulates within the cancellous bone sponge.

[0053] Example 8. Saline/Glycerol Rehydrated Cancellous Sponge Loaded with DCP in Ethanol and then Swollen with Glycerol. Demineralized cancellous cubes were hydrated with saline (0.9% NaCl) in a 35% glycerol solution, resulting in swelling of the cancellous cube. DCP was suspended in 70% ethanol as described in example 2. The DCP was introduced into the cancellous matrix using the syringe technique described above in Example 3. The resulting DCP-loaded cancellous cube was then soaked in 35% glycerol, resulting in swelling of the DCP such that it was held securely within the matrix. The swelling the DCP in place and the 'stickiness' of the glycerol acting as a binding agent were observed.

[0054] Example 9. Particle Sizes of DBM powder. DBM Powder from cortical and cancellous bone was prepared in a range of particle sizes from 100 microns to 4 mm using standard techniques for grinding and sieving. The powder was then selected to match the natural pore structure of the cancellous sponge as pore size varies with the anatomical location from where it is obtained. Subchondral (just below the joint surface) cancellous tends to be very dense with small pores, whereas cancellous further from the joint surface has larger pores. By matching the particle size of APPENDIX I  US Prov. Appln 61/877,825

72950/T668 the powder to the pore size of the cancellous matrix, i.e. large particle impregnated into large pores and vice versa, the powder appeared to be more resistant to subsequent dislodging during rehydration.

[0055] Example 10. <u>Loading of Additive to Cancellous Sponge</u>. An additive may also be incorporated into the cancellous bone sponge directly in its own suspension added by syringe as disclosed, or in suspension together with DBM powder as described herein. For example, an additive such as a perfluorocarbon may be added together with the DBM powder. A cancellous cube with DBM powder prepared according to the methodology of Example 4 was subsequently placed in a container of Perfluorotributylamine (PFTBA). The cubes of material were removed and blotted dry. The uptake of PFTBA ranged from 0.5 to 1.0 g/cm$^3$.

Example 11. Preparation of Granular Product. Cancellous bone infused with DBM powder according to the methodology of Example 4 was rough chopped to form granules < 4mm in dimension.

APPENDIX I

Attorney: Nicole Ballew Chang
Attorney Docket No. 72950/T868
First Named Inventor: Nelson L. Scarborough
Title: COMPOSITIONS OF AND METHODS FOR CANCELLOUS BONE MATRIX
Page 1/2

US Prov. Appln 61/877,825

APPENDIX I

Attorney: Nicole Ballew Chang
Attorney Docket No. 72950/T668
First Named Inventor: Nelson L. Scarborough
Title: COMPOSITIONS OF AND METHODS FOR CANCELLOUS BONE MATRIX
Page 2/2

US Prov. Appln 61/877,825

While the present invention has been illustrated and described with reference to certain exemplary embodiments, those of ordinary skill in the art will understand that various modifications and changes may be made to the described embodiments without departing from the spirit and scope of the present invention, as defined in the following claims.

What is claimed is:

1. An encapsulated 3-dimensional (3-D) bone matrix composition for inducing bone growth, comprising:
    a 3-D bone matrix selected from a demineralized cancellous sponge or a non-demineralized cancellous bone strip;
    an oxygen carrier incorporated into the 3-D bone matrix; and
    an encapsulation material that encapsulates the 3-D bone matrix.

2. The encapsulated 3-D bone matrix composition of claim 1, wherein the oxygen carrier is selected from the group consisting of perfluorodecalin, perfluorohexane, perfluoroperhydrophenanthrene, perfluorobutylamine (PFTBA or PFTBM), perfluorooctylbromide (PFOB), perfluoro-n-octane, octafluoropropane, perfluorodichlorooctane, perfluorodecane, perfluorotripropylamine, perfluorotrimethylcyclohexane, perfluoromethyladamantane, perfluorodimethyladamantane, perfluoromethyldecaline, perfluorofluorene, diphenyldimethylsiloxane, monohydroperfluorooctane, alumina-treated perfluorooctane, and mixtures thereof.

3. The encapsulated 3-D bone matrix composition of claim 1, wherein the encapsulation material is a collagen-derived material.

4. The encapsulated 3-D bone matrix composition of claim 1, further comprising a demineralized bone matrix powder mixed with the oxygen carrier.

5. The encapsulated 3-D bone matrix composition of claim 1, further comprising a dispersing agent mixed with the oxygen carrier.

6. The encapsulated 3-D bone matrix composition of claim 5, wherein the dispersing agent is selected from the group consisting of glycerols, lecithins, polyoxamers, surfactants, and phospholipids.

* * * * *